United States Patent
Zuckermann et al.

[11] Patent Number: 5,240,680
[45] Date of Patent: Aug. 31, 1993

[54] AUTOMATED APPARATUS FOR USE IN PEPTIDE SYNTHESIS

[75] Inventors: Ronald N. Zuckermann, Berkeley; Steven Banville, San Francisco, both of Calif.

[73] Assignee: Chiron Corporation, Emeryville, Calif.

[21] Appl. No.: 811,162

[22] Filed: Dec. 19, 1991

[51] Int. Cl.⁵ .................. C07K 1/08; C12M 1/00
[52] U.S. Cl. ........................... 422/67; 422/63; 422/81; 422/100; 422/101; 422/131; 422/138; 435/313; 435/316; 436/43; 436/89; 935/87; 935/88
[58] Field of Search ............ 422/67, 81, 62, 63, 422/101, 108, 100, 102, 129, 131, 138; 436/43, 52, 89, 55, 86; 435/313, 316; 935/87, 88, 85

[56] References Cited

U.S. PATENT DOCUMENTS

| | | | |
|---|---|---|---|
| 3,531,258 | 9/1970 | Merrifield et al. | 422/116 |
| 3,557,077 | 1/1971 | Brunfeldt et al. | 422/108 X |
| 3,647,390 | 3/1972 | Kubodera et al. | 422/129 |
| 4,598,049 | 7/1986 | Zelinka et al. | 422/62 |
| 4,668,476 | 5/1987 | Bridgham et al. | 422/62 |
| 4,701,304 | 10/1987 | Horn et al. | 422/62 |
| 4,746,490 | 5/1988 | Saneii | 422/62 |
| 4,835,707 | 5/1989 | Amano et al. | 364/497 |
| 4,865,992 | 9/1989 | Hach et al. | 436/51 |
| 4,879,242 | 11/1989 | Tsukioka | 436/54 |
| 5,112,575 | 5/1992 | Whitehouse et al. | 422/116 |

OTHER PUBLICATIONS

Cwirla, S. E., et al., Proc. Natl. Acad. Sci. USA 87:6378-6382 (1990).
Fodor, S. P. A., et al., Science 251:767-773 (1991).
Geysen, H. M., et al., Proc. Natl. Acad. Sci. USA 81:3998-4002 (1984).
Houghten, R. A., Proc. Natl. Acad. Sci. USA 82:5131-5135 (1985).
Tjoeng, F. S., et al., Int. J. Peptide Protein Res. 35:141-146 (1990).

*Primary Examiner*—James C. Housel
*Assistant Examiner*—Long V. Le
*Attorney, Agent, or Firm*—Peter J. Dehlinger

[57] ABSTRACT

An automated apparatus for use in cleaving, deprotecting and purifying synthesized polypeptides immobilized on solid phase particles. The apparatus includes cleavage and extraction vessels where peptide cleavage from solid-phase particles, and extraction of scavenger reagents occurs, respectively, and structure for automated transfer of (i) reaction solutions into and out of the cleavage vessel, (ii) peptide solution from the cleavage vessel to the extraction vessel, and (iii) extraction solvent into the extraction vessel, in dispersed form. Excess extraction solvent is removed from a side arm in the extraction vessel.

5 Claims, 9 Drawing Sheets

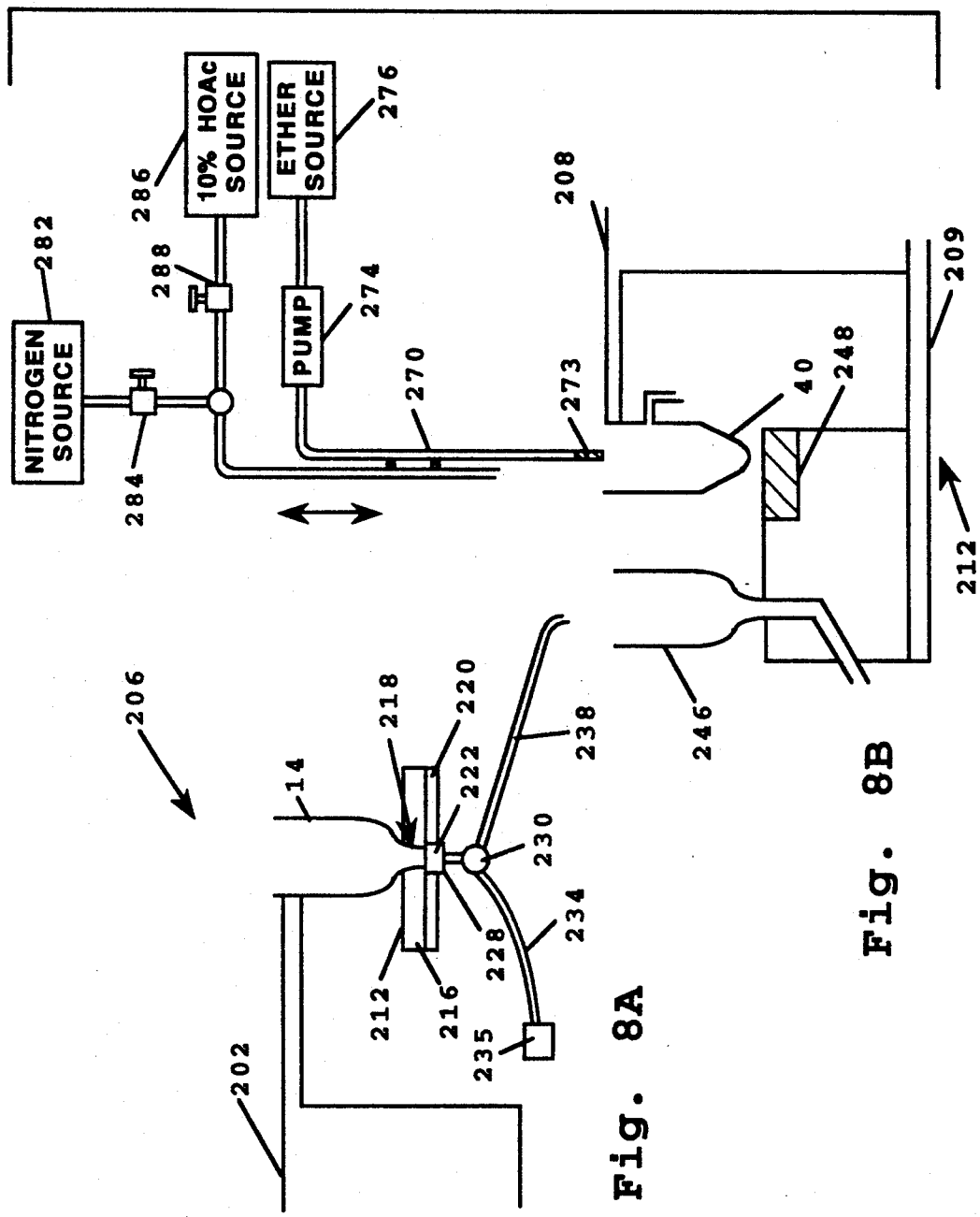

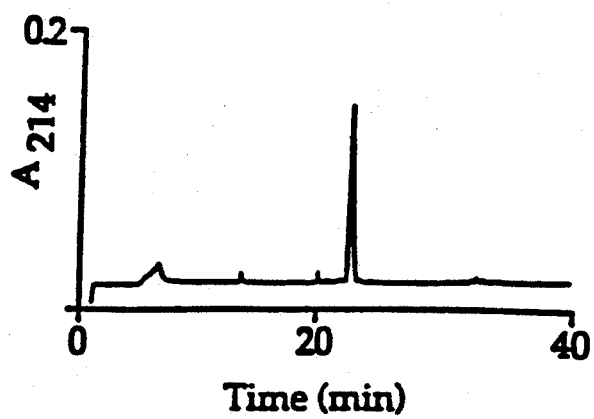
Fig. 9H
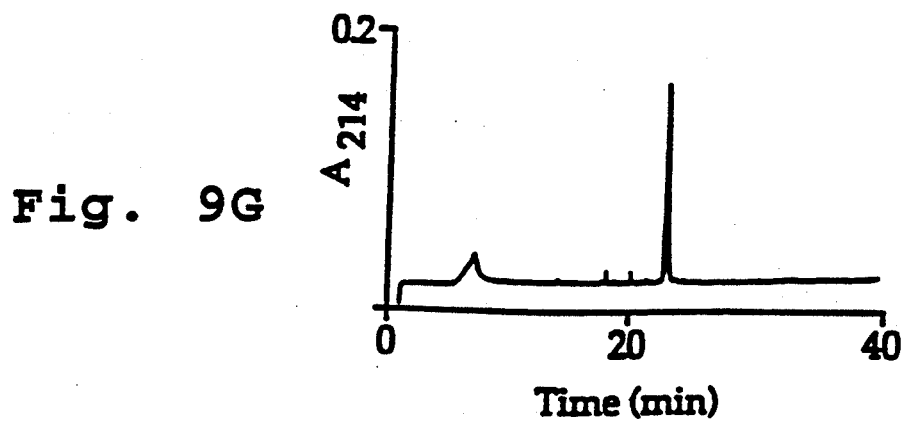
Fig. 9G
Fig. 9I
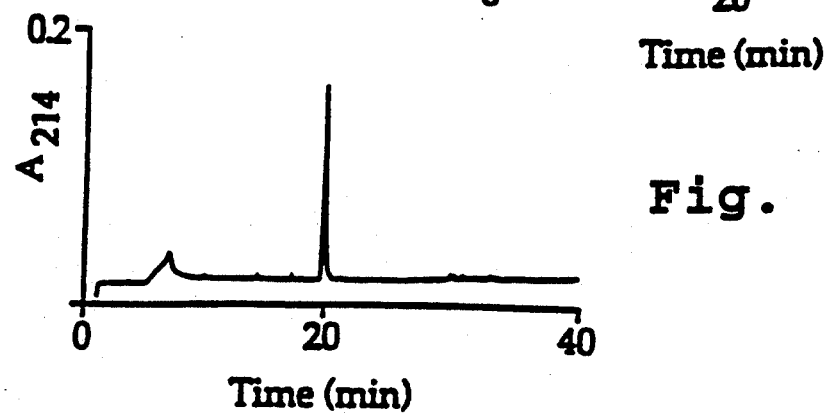
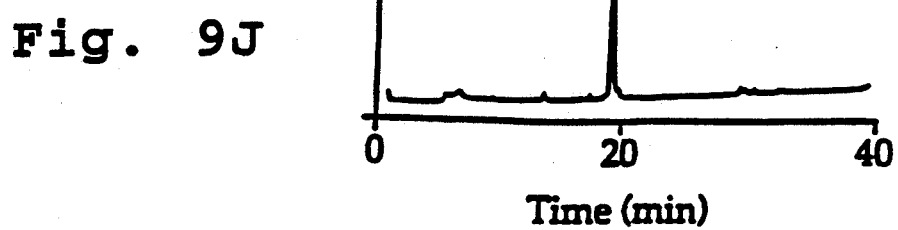
Fig. 9J

AUTOMATED APPARATUS FOR USE IN PEPTIDE SYNTHESIS

FIELD OF THE INVENTION

The present invention relates to an automated apparatus for deprotection, cleavage and purification of polypeptides and other peptide-like polymers synthesized on a resin-based, solid support medium.

REFERENCES

King, D. S. et al. A cleavage method which minimizes side reactions following FMOC solid phase peptide synthesis. Int. J. Peptide Protein Res. (1990) 36:255.

BACKGROUND OF THE INVENTION

Defined-sequence polypeptides, peptoids and other polymers are routinely synthesized by solid phase methods in which amino acids are added step-wise to a growing polypeptide chain immobilized on a solid support. One well-known method for achieving such solid-phase peptide synthesis utilizes 9-fluorenylmethoxycarbonyl (FMOC) protecting groups on the amino acids. The general chemical reagents and conditions used in such synthesis are generally referred to a "FMOC chemistry" for peptide synthesis.

Automated systems for FMOC synthesis of polypeptides and other polymers are known. However, post-synthesis processing, including (i) cleavage of peptide from the support, (ii) side-chain deprotection and (iii) removal of non-peptide contaminants, is still carried out manually, requiring significant effort and ultimately limiting the rate of synthetic polymer production. Furthermore, the reagents used to achieve these steps are toxic and often extremely foul-smelling, making manual work up procedures both hazardous and unpleasant.

In view of the foregoing, there is a need for increasing the speed and efficiency of post-synthetic workup of synthesized polypeptides and other polymers. There is also a need for achieving post-synthetic workup in a way that minimizes human exposure to toxic reagents.

SUMMARY OF THE INVENTION

The present invention includes an automated apparatus for use in cleaving, deprotecting and purifying peptide or peptide-like polymers prepared by FMOC chemistry, where the peptides are synthesized on solid-phase resin particles. The apparatus includes a cleavage vessel having an opening fitted with a filter through which a gas may be bubbled into the vessel, and an extraction vessel having an open end, a closed end defining a reservoir, and a side arm.

Also included in the apparatus are a valved gas source operable to deliver gas into said cleavage vessel through its filter opening; a valved solvent source is operable to introduce solvent into the reservoir in the extraction vessel, with excess solvent being removed from the vessel by overflow through its sidearm; and structure operable to transfer peptide solution from the cleavage to extraction vessel.

The valved fluid sources and transfer structures are controlled by a control unit which effects peptide cleavage and solvent extraction from the peptide solution in an automated fashion.

In a preferred embodiment, the transfer structure is a robotic arm also designed to transfer the particle suspension into the cleavage vessel, and predetermined reagent solutions into the cleavage vessel. In this embodiment, the robotic arm may include a spring-loaded, telescoping spigot designed for reagent delivery into the cleavage vessel.

These and other objects and features of the invention will become more fully apparent when the following detailed description of the invention is read in conjunction with the accompanying drawings.

BRIEF DESCRIPTION OF THE DRAWINGS

FIGS. 8A and 8B show, in schematic views, in partial side, cross-sectional view, of a cleavage (8A) and extraction (8B) station in the FIG. 7 apparatus, and FIGS. 9A-9J are reverse-phase HPLC chromatograms of ten selected decapeptides cleaved, deprotected and extracted using the robotic arm embodiment of the apparatus of the invention.

DETAILED DESCRIPTION OF THE INVENTION

I. Automated Cleavage, Deprotection and Purification Apparatus

Figure 1:
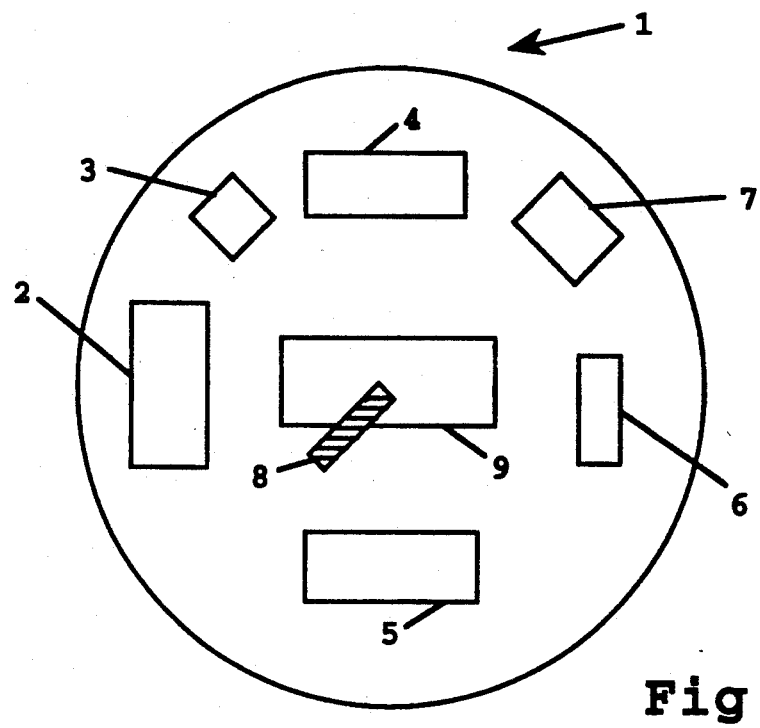
FIG. 1 is a diagrammatic plan view of an apparatus constructed according to one embodiment of the invention.

FIG. 1 is a diagrammatic view of an automated apparatus 1 for cleavage, deprotection and purification of solid-phase bound synthetic polypeptides. The system includes a polypeptide synthesis station 2, a cleavage station 3, an extraction station 4, a cleavage vessel rack 6, an extraction tube rack 7, and a robotic arm 8 connected to a control unit 9 which automates and directs the robotic arm transfer activities between the various stations. The design and functioning of the control unit will become clear from the operation of the system described below.

Polypeptide synthesis is accomplished in the synthesis station 2 utilizing conventional FMOC chemistry. In the present invention, solid-phase polypeptide synthesis employing discrete particles, such as polystyrene beads, is preferred. Briefly, synthesis is accomplished by derivitizing such particles with a selected N-protected amino acid according to conventional derivitization methods. The particles are then suspended in a suitable suspension liquid that is substantially isopycnic with the solid-phase medium to form a stable particle-suspension mixture of substantially uniform particle density. Selected amino acids are added to the N-terminus of the particle bound amino acid or polypeptide in a desired sequence, according to conventional methods, until the desired polypeptide sequence is synthesized.

Although the apparatus is described herein with reference to polypeptide synthesis, polymer synthesis of any other peptide-like polymers by FMOC chemistry is also contemplated.

After peptide synthesis is completed, the suspension of particles containing the attached polypeptides is transferred by robotic arm 8 to cleavage station 3 where the polypeptide is cleaved from the solid support and deprotected, as will be further described below, yielding a trifluoroacetic acid solution of the desired polypeptide and residual reagents used in the cleavage/deprotection process. The polypeptide solution is then transferred by the robotic arm to the extraction station 4 where the polypeptide is evaporated, dissolved in aqueous acetic acid and purified using a water-immiscible solvent to remove solvent extractable compounds, such as reagent residues.

Figure 2:
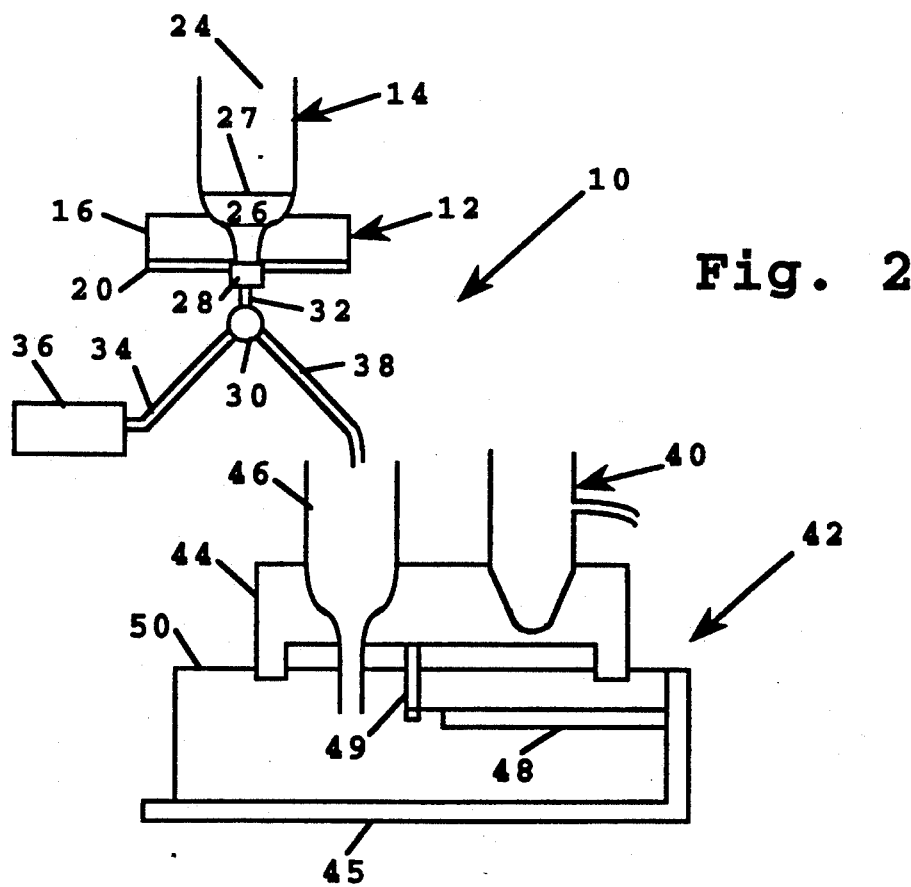
FIG. 2 is a schematic view, shown in partial side, cross-sectional view, of cleavage and extraction stations in the FIG. 1 apparatus.
Figure 3:
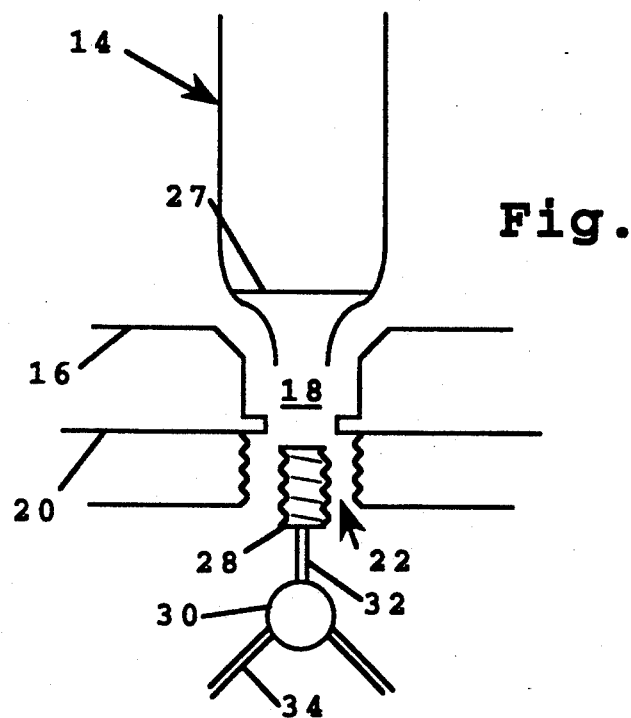
FIG. 3 is an enlarged, exploded cross-sectional view of the cleavage vessel and the cleavage vessel platform of the embodiment of FIG. 1.

Turning to FIGS. 2 and 3, the cleavage station 10 of the invention will now be described. Cleavage station 10 includes a cleavage vessel platform 12 for receipt of a cleavage vessel 14. Cleavage vessel 14 is substantially cylindrical for most of its length and is provided with an opening 24 at one end and is narrowed into a funnel ending in an opening 26 fitted with a filter 27 on the opposite end. Although the cleavage vessel of the invention may be of any composition and construction suitable for the cleavage and deprotection techniques described herein, disposable polypropylene tubes of 15 Ml capacity fitted with a 20 μM polypropylene frit are preferred and are available from Varian Sample Preparation Products (Harbor City, Calif.).

Cleavage vessel platform 12 is comprised of an upper plate 16 joined by conventional means to a lower plate 20. Plates 16 and 20 are provided respectively with throughholes 18 and 22 that together form a continuous channel through the plates when joined. Throughhole 18 is configured for the snug, water-tight receipt of the funniliform (Luer taper tip) end of cleavage vessel 14, whereas throughhole 22 is configured for snug receipt of a threaded plug 28. Plug 28 is connected to a three-way valve 30 via tubing 32. Three-way valve 30 is connected via tubing 34 to a source 36 of substantially inert gas, nitrogen is preferred, and is connected to the remainder of the apparatus via tubing 38.

Cleavage and deprotection are accomplished simultaneously by delivery of a batch of the suspension of particle-bound bound polypeptides and appropriate reagents, described further below, to a cleavage vessel previously transferred by the robotic arm from the cleavage vessel rack to the cleavage vessel platform. The suspension and reagents are reacted by mixing them with bubbling gas which is delivering from gas source 36 into the cleavage vessel through opening 26.

Once cleavage and deprotection are complete, the peptide-bearing solution is passed out of cleavage vessel 14 into extraction tube 40 onto collection rack 42, which is provided with a mount 44 for holding extraction tube 40 in one position and a waste receptacle 46. Mount 44 is horizontally and slidably coupled to a track 50 which is attached to an extraction rack base 45. The extraction rack is also provided with a pneumatic air cylinder 48 which is coupled to a portion of rack base 45 at one end and to a bracket 49 at the other end. Bracket 49 is slidably mounted on track 50 and non-movably coupled to the bottom of mount 44. Delivery of air to air cylinder 48 causes bracket 49 to move, thereby effecting movement of mount 44 along the axis of track 50. The position of mount 44, and by extension the positions of extraction tube 40 and waste receptacle 46, may thus be adjusted with respect to the position of the end of tubing 38. Thus, it will be appreciated that delivery of the contents of cleavage vessel 14 can be directed to either the extraction tube or the waste receptacle as desired.

Figure 6:
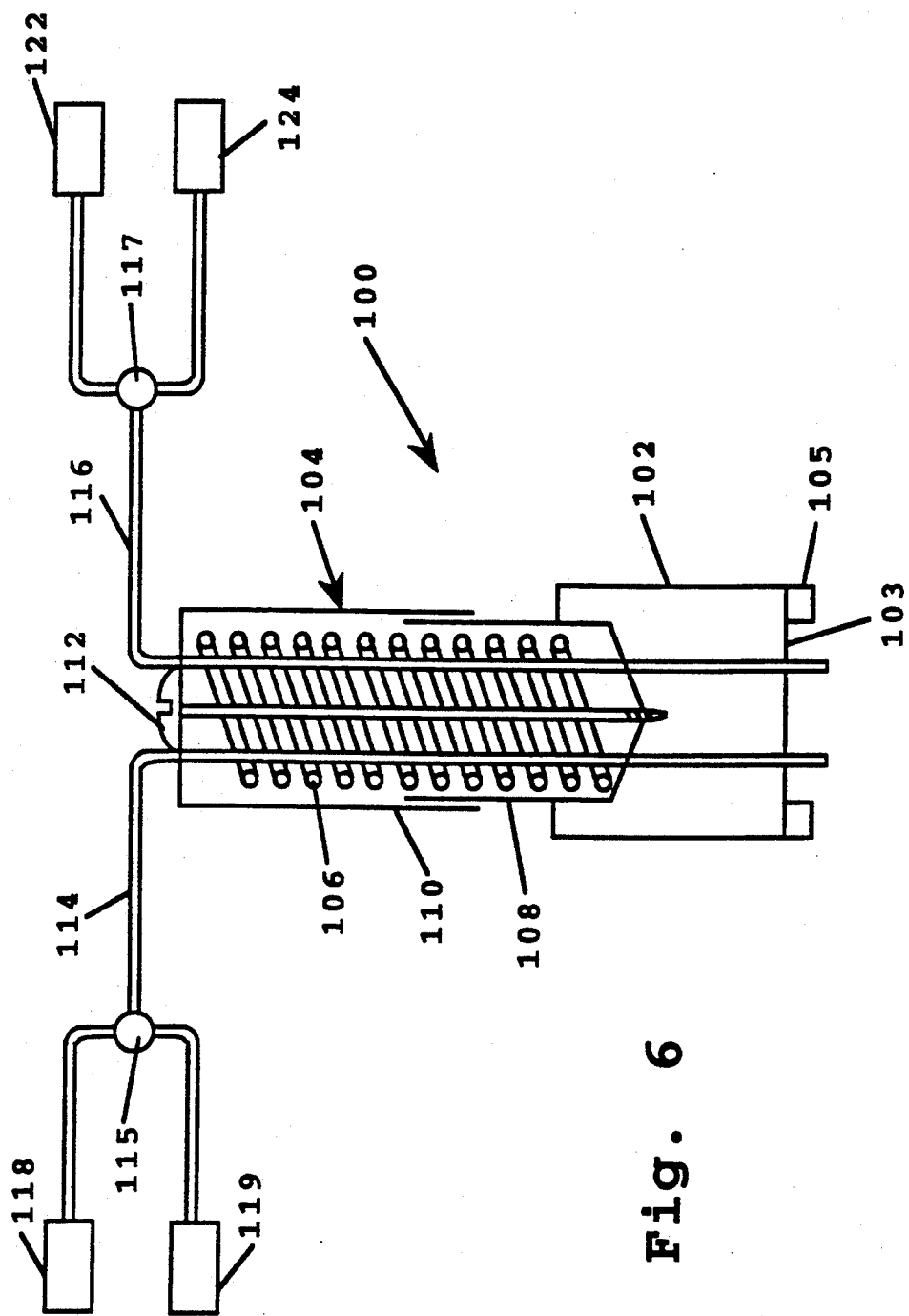
FIG. 6 is a cross-sectional view of spigot structure in one embodiment of the invention.

The spigot 100, as shown in FIG. 6, will now be described. Spigot 100 comprises a plug 102 connected to a spring-loaded, telescoping member 104. Telescoping member 104 includes a spring 106 surrounded in below by an inner sheath 108 and above by an outer sheath 110 which is received over a portion of inner sheath 108. Telescoping member 104 is held together in extended position by a fastener 112 over which sheath 110 can slide. Fastener 112 further operates to secure the telescoping member to plug 102. Plug 102 is tapered to an end 103 that is provide with a foam collar, preferably composed of polyethylene foam, distributed circumferentially around the edge of end 103. Collar 105 cooperates with plug 102 to provide an airtight seal when spigot 100 is pressed on top of the cleavage vessel. The spigot is further supplied with tube leads 114 and 116 to both a pressurized TFA source 118 and a pressurized scavenger cocktail source 119. Tube lead 114 is connected to a valve 115 which is connected in turn to pressurized reagent sources 118 and 119. Tube lead 116 is connected to a valve 117 which is in turn connected to both a nitrogen source 122 and a pressurized $CH_2Cl_2$ source 124. Spigot 100 can be used to deliver selected reagents to cleavage vessel 14. Spigot 100 can also be used to evacuate fluids from the cleavage vessel by plugging the cleavage vessel with plug 102 thereafter pressurizing the vessel with nitrogen from nitrogen source 122 to force fluid out.

Figure 4:
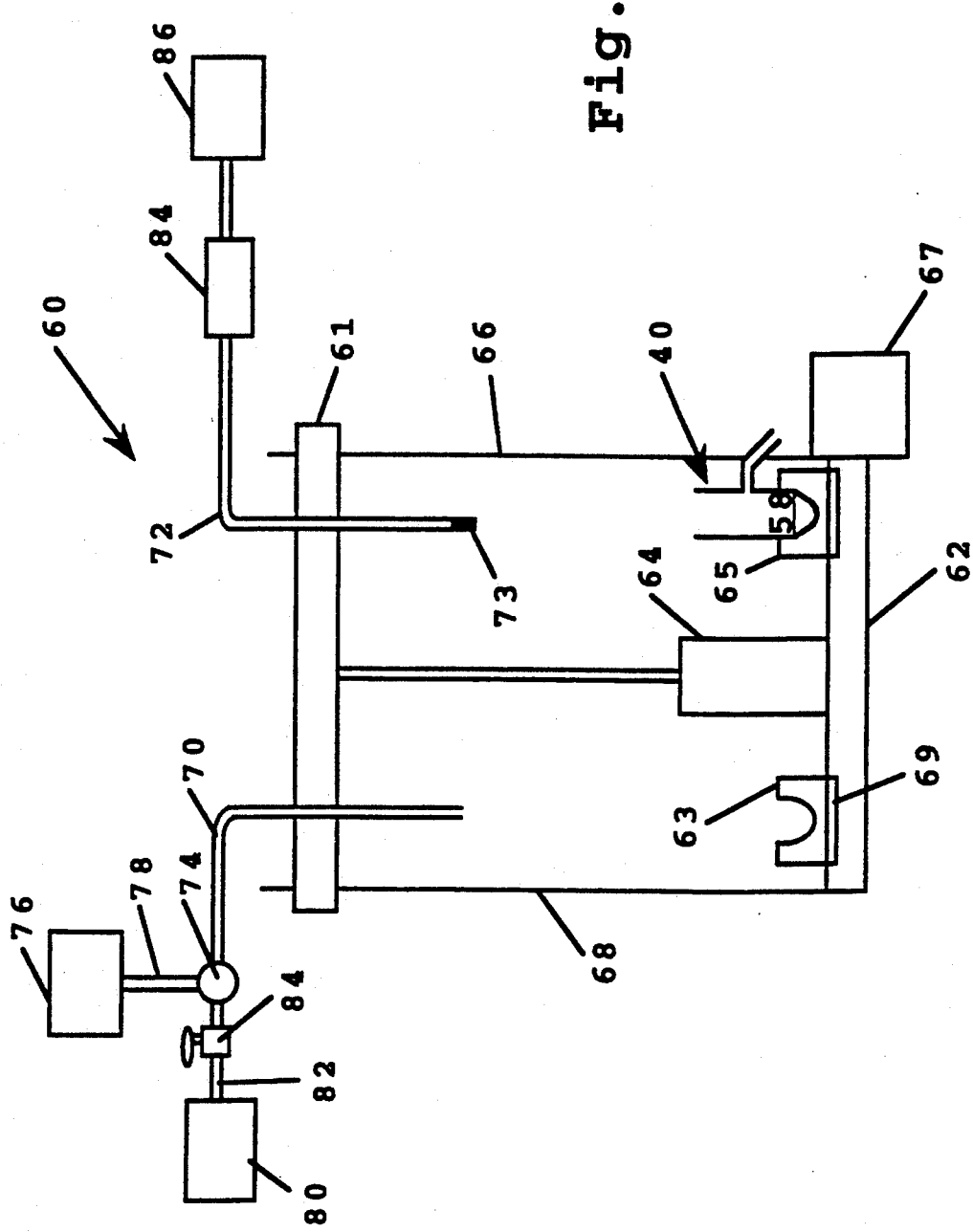
FIG. 4 is an enlarged cross-sectional view of the extraction station of the embodiment of FIG. 1.
Figure 5:
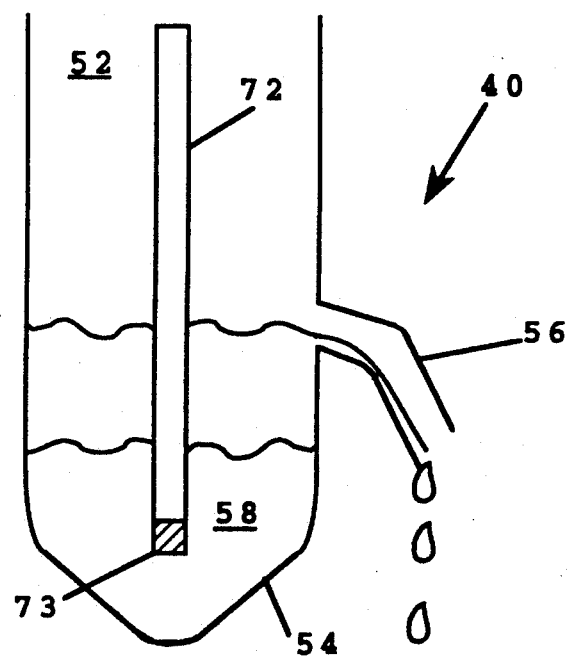
FIG. 5 is an enlarged cross-sectional view of the extraction tube and extraction solvent delivery tube in the extraction station.

Turning now to FIGS. 4 and 5, the extraction station 60 of the present invention will now be described. Extraction tube 40 is substantially cylindrical in shape that is provided with an open end 52 and a closed end 54. The closed end is more or less conical in shape as opposed to some other configuration such as being hemispheric or flattened. Extraction tube 40 is further provided with a tubular side arm 56 positioned on the side of the tube at a selected distance between the two ends. Because fluid can flow out of the extraction tube through the side arm, the position of side arm 56 thus defines a reservoir 58 of 20 mL capacity within the closed end of extraction tube 40 when the extraction tube is positioned with its closed end facing downward. Any suitable extraction tube having the configuration above may be used, but glass extraction tubes are preferred.

Extraction station 60 includes an extraction tube platform 62, an air cylinder 64 vertically positioned on an extraction tube platform 62, a crossbar 61 connected to air cylinder 64 and disposed parallel to the plane of an extraction tube platform 62, and substantially rigid guides 66 and 68 connected to an extraction tube platform 62 in fixed relation and slidably extending through crossbar 61. Extraction tube platform 62 is provided with two receptacles 63 and 65 on opposite sides of air cylinder 64, each configured for snug receipt of the closed end of an extraction tube. Receptacle 63 is provided with a heating element 69 capable of heating extraction tube 40 and its contents when positioned within the receptacle. The heating element is comprised of any suitable metal, such as aluminum, around which several lengths of nichrome heating wire are wound. Receptacle 65 is positioned proximate to a waste receptacle 67 so that waste solvent that passes from the side arm of extraction tube 65 can be deposited in waste receptacle 67.

Crossbar 61 can be raised or lowered relative to the extraction tube platform 62 by delivering or removing air from air cylinder 64. The alignment of crossbar 61 relative to extraction tube platform 62 is maintained by rigid guides 66 and 68 around which crossbar 61 passes as it is raised and lowered.

Connected to the crossbar are tube leads 70 and 72. Tube lead 70 extends to a three-way valve 74 that is in turn connected to a nitrogen source 76 via tube 78 and to a 10% acetic acid source 80 via tube 82, with a stop cock 84 positioned along tube 82 between aqueous acetic acid source 80 and three-way valve 74. Tube lead 72 extends to a pump 84 that is in turn connected to an ether source 86, and is provided with a fritted tip 73. Pump 84 is preferably a diaphragm pump and can be obtained from ProMinent Fluid Controls, Inc. (Pittsburgh, Pa.).

Operation of the apparatus is accomplished using control unit 9, which operates robotic arm 8 and air cylinders 48 and 64, and mediates the delivery of reagents and gasses (via the activation of solenoid valves) to cleavage vessel 14 and extraction tube 40.

The robotic arm is mounted on a head (not shown) which is rotatable along an axis for raising and lowering the arm. The distal end of the arm is designed for pick up and release of the cleavage vessel, extraction tube and spigot. One preferred type of robotic device is a Zymate XP robot supplied commercially from Zymark Corp. (Hopkinton, Mass.). The delivery unit in the apparatus is a Zymark "general purpose" hand (not shown) which has two fingers that are capable of grabbing the spigot, cleavage vessel or extraction tube and carrying it to a selected position within either the cleavage or extraction station. The robotic arm and associated delivery units are also referred to herein as transfer means.

The control unit in the apparatus is a microprocessor which is programmed to direct the control of the robotic arm and air cylinders and to actuate delivery of reagents and gasses (via solenoid valve activation) according to user-specified settings.

Figure 7:
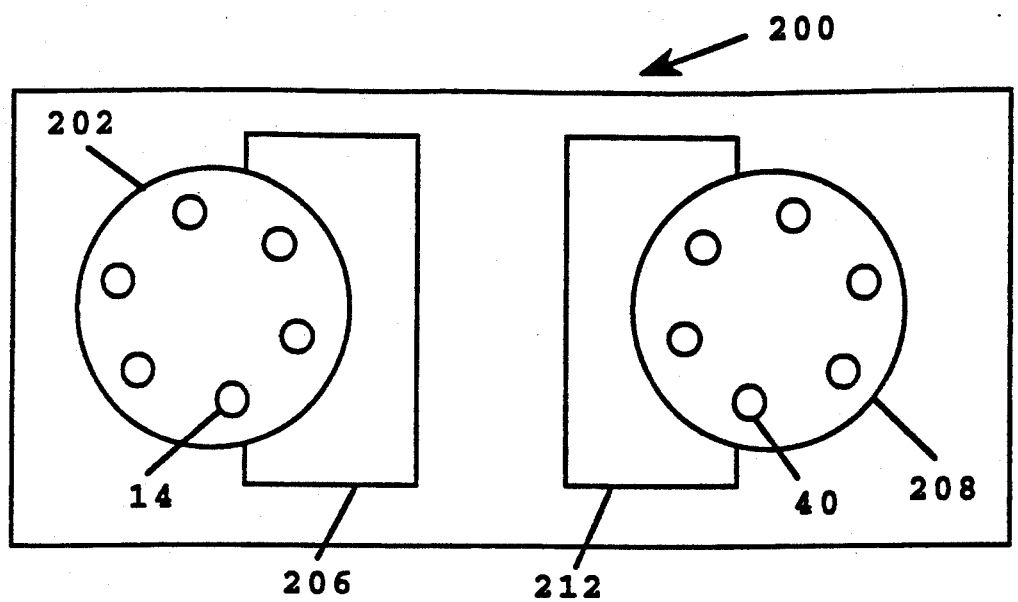
FIG. 7 is a diagrammatic plan view of a second embodiment of the apparatus of the invention.
Figure 10:
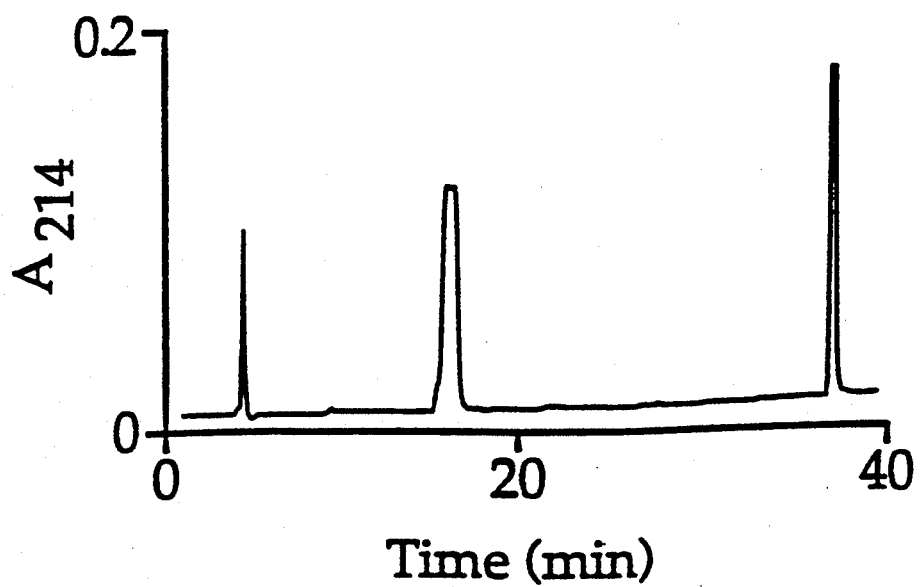
FIG. 10 is a reverse-phase HPLC chromatogram of the scavenger cocktail used in the cleavage and deprotection of polypeptides according to the invention.
Figure 9A:
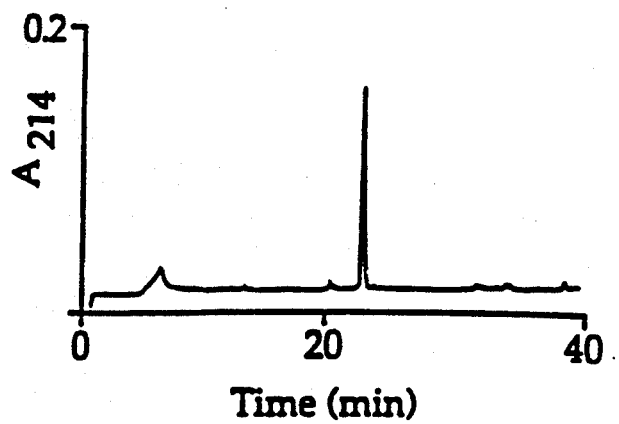
Figure 9B:
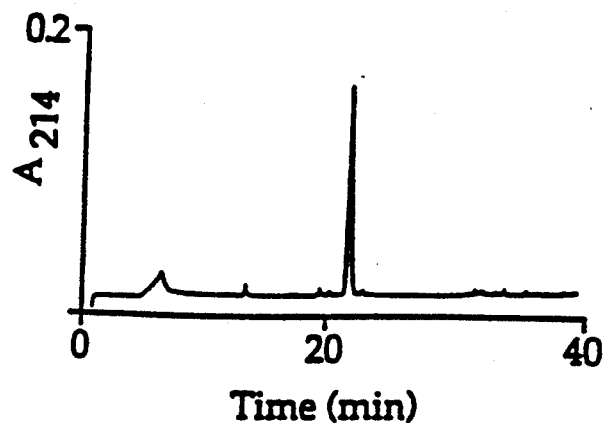
Figure 9C:
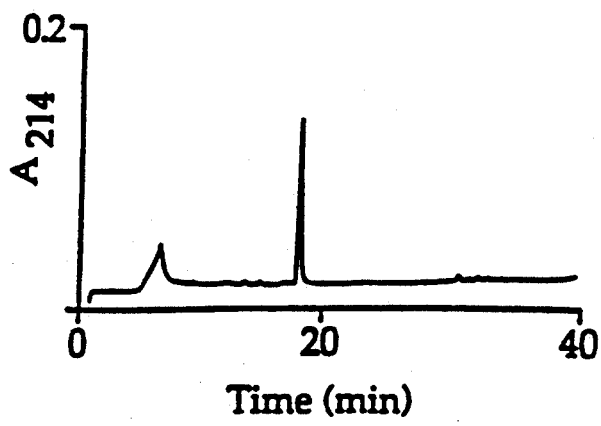
Figure 9D:
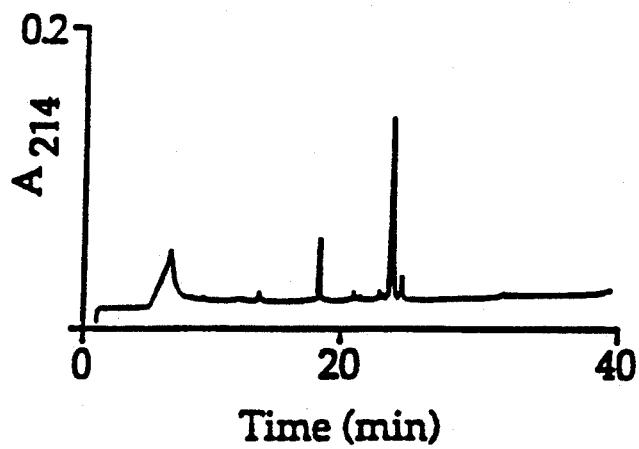
Figure 9E:
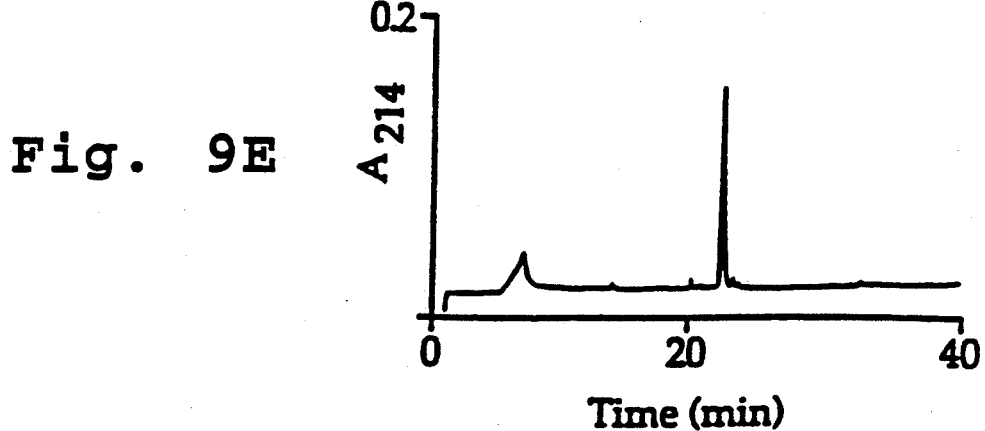
Figure 9F:
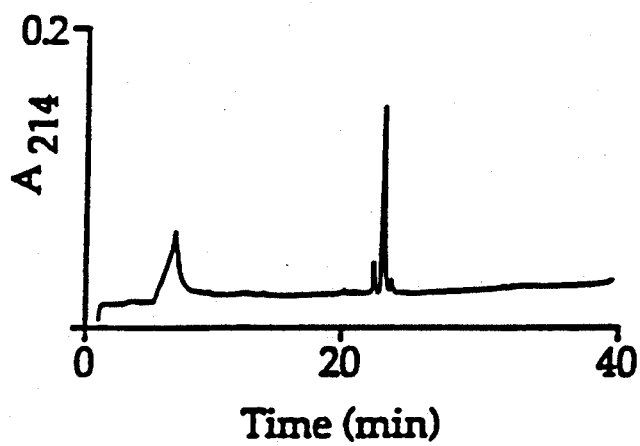

Turning now to FIGS. 7, 8A and 8B, an alternate embodiment of the invention will now be described. The setup is similar to the apparatus described above, except that the robotic arm has been substituted by a rotating carousel and the cleavage and extractions stations are connected by a valved tube for direct transfer of the cleaved, deprotected peptide solution between stations. According to this embodiment, an automated apparatus 200 is provided and includes a cleavage vessel carousel 202 carrying a plurality of cleavage vessels 14 positioned to rotate individual tubes over the cleavage station 206 (FIG. 8A) and an extraction tube carousel 208 carrying a plurality of extraction tubes 40 positioned to rotate individual tubes over the extraction station 212. (FIG. 8B.

With respect to FIG. 8A, cleavage station 206 includes a cleavage vessel platform 212 for receipt of a cleavage vessel 14. Cleavage vessel platform 212 is comprised of an upper plate 216 joined by conventional means to a lower plate 220. Plates 216 and 220 are provided respectively with throughholes 218 and 222 that together form a continuous channel through the plates when joined. Throughhole 218 is configured for the snug, water-tight receipt of the funniliform (Luer taper tip) end of cleavage vessel 14, whereas throughhole 222 is configured for snug receipt of a threaded plug 228. Plug 228 is connected to a three-way valve 230 via tubing 232. Three-way valve 230 is connected via tubing 234 to a source 235 of substantially inert gas, nitrogen is preferred, and is connected to the remainder of the apparatus via tubing 238.

Cleavage and deprotection are accomplished as described above. Once cleavage and deprotection are complete, the peptide-bearing solution is passed out of cleavage vessel 14 into extraction tube 40, which is positioned in extraction station 212 by carousel 208. Carousel 208 is positioned on a slidable rack 209, which is provided with a waste receptacle 246. It will be appreciated that the lateral position of extraction station 212 may thus be adjusted so that the end of tubing 238 can be aligned with either of extraction tube 40 or with waste receptacle 246 for delivery of the contents of cleavage vessel 14.

With respect of FIG. 8B, extraction station 212 is further provided with a heating element 248 capable of heating extraction tube 40 and its contents when the tube is positioned above the heating element. The heating element is of any common type capable of delivering heat to the end of extraction tube 40 sufficient to heat the contents of the tube to a temperature of at least 30° C.

Extraction station 212 is further provided with a tube lead 270 fitted with a fritted tip 273. Tube lead 270 is connected through a pump 274 to an ether source 276. A second tube 278 is connected through a three-way valve 280 that is ultimately connected to a nitrogen source 282 via valve 284 and to a 10% aqueous acetic acid source 286 via a valve 288. Also included in the extraction station is moving means (indicated by arrow 290) for moving tubes 270 and tube 278 in and out of operative positions in the extraction tube.

Operation of the apparatus is accomplished using a control unit designed to operate carousel 202 and 208 and to mediate the delivery of reagents and gasses to cleavage vessel 14 and extraction tube 40.

II. Automated Cleavage, Deprotection and Purification Method

The apparatus of the invention may be used for cleavage, deprotection and purification of solid-phase bound synthetic polypeptides according to another aspect of the invention. The method will first be described with reference to the embodiment that incorporates a robotic arm, as described above and illustrated in FIGS. 1–6.

Both the apparatus and method of the invention are based on cleaving, deprotecting and purifying polypeptides synthesized using FMOC chemistry. Immediately after the synthesis, the fully protected peptide-resin particles are suspended in an isopycnic solvent (60% 1,2-dichloroethane/dimethylformamide). The first step of the method is delivery of the entire amount of the particle suspension to the cleavage vessel that has been transferred from the cleavage vessel rack to the cleavage vessel platform.

In the next step of the method, $CH_2Cl_2$ is transferred from the multi-spigot to the particles in the cleavage vessel to wash any residual dimethylformamide that remains from the resin-transfer process. The plug of the spigot is then pressed on top of cleavage vessel and nitrogen thereafter introduced to evacuate the wash solution from the vessel. The support particles are then dried by rinsing with $CH_2Cl_2$ and blowing with nitrogen both delivered from the spigot.

Cleavage and deprotection of the polypeptides are achieved by delivering triflouroacetic acid (TFA), preferably as a 96% TFA/4% $H_2O$ solution, and a mixture of scavenger reagents from the spigot into the cleavage vessel holding the dried particles. TFA achieves both cleavage and deprotection while the scavenger reagents prevent unwanted side reactions that may alter the chemical structure of R-groups of the individual amino acids or the structure of the polypeptide itself. A suitable scavenger reagent is a cocktail of ethanedithiol, thioanisole and phenol in a 1:2:2 ratio. An inert gas, such as nitrogen, is delivered at selected intervals through the base of the cleavage vessel and allowed to bubble up through the particle slurry to promote mixing. Completion of the cleavage/deprotection process yields a solution containing the synthesized polypeptides, scavengers and reaction by-products. The spigot is then used to deliver nitrogen to the cleavage vessel to evacuate the polypeptide solution. If desired, the solid particles may be washed after cleavage and evacuation with more TFA, which is evacuated and collected with the polypeptide solution sample.

During or upon completion of cleavage and deprotection, the robotic arm moves an extraction tube from the extraction tube rack to the collection rack of the cleavage station. The air cylinder is then used to position the collection rack so that the extraction tube is positioned beneath tube 38 to receive the polypeptide solution evacuated from the cleavage vessel.

In the next step, the robotic arm moves the extraction tube containing the polypeptide solution to receptacle 63 on the extraction tube platform. The air cylinder is then used to lower to crossbar over the extraction tube, thereby bringing the end of tube lead 70 within the extraction tube. TFA in the polypeptide solution is then evaporated, using low heat (preferably 30°-40° C.) delivered by receptacle 63 and a stream of nitrogen gas delivered by tube lead 70. The residual liquid remaining after evaporation, a mixture of the synthesized polypeptides and residual scavenger reagents, are suspended in an aqueous acidic solution (preferably a 10% aqueous acetic acid solution) delivered to the extraction tube through tube lead 70. A uniform suspension is obtained by bubbling nitrogen gas through the solution via tube 70. The crossbar is now raised and the extraction tube moved by the robotic arm to receptacle 65 on the extraction tube platform. The crossbar is then once again lowered to deliver tube lead 72 to the bottom or reservoir 58 within the extraction tube for delivery of the extraction solvent.

In the extraction step, a selected water-immiscible solvent, such as diethyl ether or methyl t-butyl ether, is introduced to the acidified polypeptide solution at the base of the extraction tube via tube lead 72 which is fritted at the end to distribute the solvent as evenly as possible through the acidified polypeptide solution. The solvent is preferably introduced at a controlled rate of 2-3 mL minute. As solvent is passed through the peptide solution, solvent extractable compounds, such as scavenger reagent residues, are removed and transported to a solvent layer above the peptide solution. As the solvent layer grows, it eventually overflows into the side arm and passes to a waste receptacle adjacent to the extraction tube. After extraction is complete, the cross bar is once again lifted using the pneumatic air pump and the extraction tube containing the purified polypeptide solution is removed by the robotic arm and placed in a storage rack. It will be appreciated that controlled continuous delivery of a reaction solvent to produce a continuous liquid-liquid phase extraction permits efficient extraction while reducing loss of polypeptide and minimizing possible cross-contamination of the sample. The peptide is thus provided as an aqueous solution ready for lyophilization or other uses.

The method just described is modified as follows when carried out with the carousel-based embodiment of the apparatus, described above and shown in FIG. 7.

N-terminal protected and resin-bound polypeptides are added in a desired amount to each of the cleavage vessels carried by the cleavage vessel carousel. The carousel is then activated to deliver the first of the cleavage vessels to platform 202 of cleavage station 206. Rinsing, drying, deprotection and cleavage of the polypeptide proceeds as described above.

Upon completion of the cleavage and deprotection reactions, nitrogen is delivered via the multi-spigot 100 to force the aqueous solution of polypeptides, TFA and scavengers through tubing 238 to extraction tube 40, which has been rotated into its proper position by extraction tube carousel 208.

Once in the extraction tube, the polypeptides are extracted as described above by evaporating the TFA, resuspending the viscous residue in aqueous acetic acid and then extracting the scavenger compounds by bubbling a selected water-immiscible solvent, such as diethyl ether or methyl t-butyl ether through the solution. Once extraction is complete, the extraction tube carousel is rotated to bring an unused extraction tube into position to receive a new batch of cleaved, deprotected polypeptide for extraction. The control unit is programmed to continue rotation until each batch of resin-bound polypeptide has been processed. Upon completion, the extraction tubes are removed from the carousel and the polypeptides recovered. The apparatus is then readied for processing another batch by filling new cleavage vessels with resin and placing unused tubes in the extraction tub rack.

From the foregoing, it will be appreciated how the objects and features of the invention are met. The automated apparatus and method of the invention permit the rapid cleavage and deprotection of FMOC-synthesized polypeptides followed by extraction of unwanted compounds used to achieve deprotection under automated conditions that both control reaction processes and optimize delivery and transfer of reagents and reactants. The apparatus and method permit a more repeatable and consistent yield polypeptide than is possible with manual methods. Finally, the apparatus and method permit the process to be carried out in an enclosed space, thereby reducing human contact with dangerous, toxic reagents.

The following examples illustrates deprotection, cleavage and extraction of synthesized polypeptides using the method and the robotic arm embodiment of the apparatus of the invention. They are intended to illustrate, but not limit, the scope of the invention.

EXAMPLE 1

Peptide Yield

Ten different decapeptides were synthesized using standard FMOC synthesis techniques on a TFA-labile Rink amide resin. The decapeptides had the following ten sequences:
(a) Ac-AAFHTTGRII-NH$_2$
(b) Ac-RAFHTTGRII-NH$_2$
(c) Ac-RAAHTTGRII-NH$_2$
(d) Ac-RAFATTGRII-NH$_2$
(e) Ac-RAFHATGRII-NH$_2$
(f) Ac-RAFHTAFRII-NH$_2$
(g) Ac-RAFHTTARII-NH$_2$
(h) Ac-RAFHTTGAII-NH$_2$
(i) Ac-RAFHTTGRAI-NH$_2$
(j) Ac-RAFHTTGRIA-NH$_2$ resin-bound samples of each decapeptide cleaved by hand and by the automated method of the invention. The individual yields of each peptide, obtained after lyophilization, were averaged together and are reported in Table I.

TABLE I

COMPARISON OF POLYPEPTIDE YIELDS COMPARING MANUAL AND AUTOMATED METHODS

| Method | Average Resin Weight (mg) | Average Peptide Weight (mg) | Average Weight |
|---|---|---|---|
| manual | 200 | 44 | 22% |
| automated | 200 | 35 | 18% |

These results demonstrate that yields similar to those obtained by manual techniques can be obtained through automated techniques.

EXAMPLE 2

Peptide Purity

The purity of the peptides obtained in the cleaved samples produced in Example 1 were analyzed by analytical reverse-phase C18 HPLC. The results for each decapeptide are reported in FIG. 8 according to the letter assigned to them in Example 1. The scavenger cocktail used in the cleavage/deprotection method of the invention was also analyzed by reverse-phase C18 HPLC under the same conditions used to analyze the decapeptides. The results of that analysis are reported in FIG. 9. It is clear from a comparison of the chromatograms that essentially all of the scavenger compounds have been removed by the extraction process of the invention.

Although the invention has been described with respect to a particular apparatus and method for cleaving, deprotecting and purifying polypeptides synthesized on a particulate solid support, it will be appreciated that various modifications of the apparatus and method are possible without departing from the invention.

It is claimed:

1. An automated apparatus for use in cleaving, deprotecting and purifying polymers prepared by FMOC chemistry, and immobilized on solid phase particles in a particle suspension, said apparatus comprising, in operative condition:

(a) a cleavage vessel having a first opening for receiving the particle suspension and a second opening fitted with a filter through which a gas may pass into said vessel to produce mixing of the suspension by bubbling and through which a solution containing polypeptides may pass out said vessel with retention of said solid phase particles;

(b) means for delivering a gas into said cleavage vessel through the second opening;

(c) an extraction vessel having an open end, a closed end defining a reservoir, and a side arm located between the two ends of the extraction vessel;

(d) transfer means for transferring a polypeptide solution produced by cleavage of said polymers from said solid-phase particles from said cleavage vessel to said extraction vessel;

(e) means for delivering a dispersion of a water-immiscible extracting solvent into polypeptide solution contained in the reservoir of said extraction vessel, with excess solvent in the extraction vessel being removed by overflow into the vessel's side arm; and (f) control means operatively connected to said gas-delivering means, said transfer means, and said solvent-delivering means, to effect (i) bubbling of gas through the particle suspension in said cleavage vessel, (ii) transfer of peptide solution from the cleavage to the extraction vessel, and (iii) delivery of a water-immiscible solvent through the polypeptide solution into the extraction vessel.

2. The apparatus of claim 1, wherein said transfer means further includes means for transferring the particle suspension into the cleavage vessel, and means for transferring predetermined reagent solutions into said cleavage vessel.

3. The apparatus of claim 2, wherein the transfer means is a robotic arm.

4. The apparatus of claim 3, wherein the transfer means includes a spigot connected to said robotic arm, said spigot comprising:

(a) a resilient plug having a first end and tapered to a second end having a foam disposed circumferentially along the edge of the second end, said plug proportioned for air-tight receipt within the first opening of said cleavage vessel;

(b) a spring-loaded, telescoping member connected to said first end of said plug; and (c) tube means passing through said telescoping member and said resilient plug, said tube means capable of selective delivery of one of several desired reagents.

5. An automated apparatus for use in cleaving, deprotecting and purifying polymers prepared by FMOC chemistry, and immobilized on solid phase particles in a particle suspension, said apparatus comprising, in operative condition:

(a) a cleavage vessel having a first opening for receiving the particle suspension and a second opening fitted with a filter through which a gas may pass into said vessel to produce mixing of the suspension by bubbling and through which a solution containing polypeptides may pass out said vessel with retention of said solid phase particles;

(b) means for delivering a gas into said cleavage vessel through the second opening;

(c) an extraction vessel having an open end, a closed end defining a reservoir, and a side arm located between the two ends of the extraction vessel;

(d) transfer means for transferring a polypeptide solution produced by cleavage of said polymers from said solid-phase particles from said cleavage vessel to said extraction vessel, said transfer means including means for transferring the particle suspension into the cleavage vessel, and means for transferring predetermined reagent solutions into said cleavage vessel, said transfer means including a robotic arm and a spigot connected to said robotic arm, said spigot comprising (i) a resilient plug having a first end and tapered to a second end having a foam disposed circumferentially along the edge of the second end, said plug proportioned for air-tight receipt within the first opening of said cleavage vessel; (ii) a spring-loaded, telescoping member connected to said first end of said plug; and (iii) tube means passing through said telescoping member and said resilient plug, said tube means capable of selective delivery of one of several desired reagents;

(e) means for delivering a dispersion of a water-immiscible extracting solvent into polypeptide solution contained in the reservoir of said extraction vessel, with excess solvent in the extraction vessel being removed by overflow into the vessel's side arm; and (f) control means operatively connected to said gas-delivering means, said transfer means, and said solvent-delivering means, to effect (i) bubbling of gas through the particle suspension in said cleavage vessel, (ii) transfer of peptide solution from the cleavage to the extraction vessel, and (iii) delivery of a water-immiscible solvent through the polypeptide solution into the extraction vessel.

* * * * *